(12) United States Patent
Luebke et al.

(10) Patent No.: US 9,834,494 B2
(45) Date of Patent: Dec. 5, 2017

(54) METHODS AND APPARATUSES FOR HYDROCARBON PRODUCTION

(71) Applicant: UOP LLC, Des Plaines, IL (US)

(72) Inventors: Charles P. Luebke, Mount Prospect, IL (US); Bart Dziabala, Hickory Hills, IL (US); Belma Demirel, Clarendon Hills, IL (US)

(73) Assignee: UOP LLC, Des Plaines, IL (US)

( * ) Notice: Subject to any disclaimer, the term of this patent is extended or adjusted under 35 U.S.C. 154(b) by 320 days.

(21) Appl. No.: 14/499,663

(22) Filed: Sep. 29, 2014

(65) Prior Publication Data

US 2016/0090335 A1 Mar. 31, 2016

(51) Int. Cl.
  *C07C 5/05* (2006.01)
  *C07C 7/163* (2006.01)
  *B01J 8/04* (2006.01)

(52) U.S. Cl.
  CPC .............. *C07C 5/05* (2013.01); *B01J 8/0457* (2013.01); *C07C 7/163* (2013.01); *B01J 2219/0004* (2013.01); *B01J 2219/00038* (2013.01); *B01J 2219/00105* (2013.01); *C07C 2521/04* (2013.01); *C07C 2523/44* (2013.01); *C07C 2523/755* (2013.01)

(58) Field of Classification Search
  CPC .................................. C07C 7/163; C07C 5/05
  See application file for complete search history.

(56) References Cited

U.S. PATENT DOCUMENTS

| | | | |
|---|---|---|---|
| 3,441,626 A * | 4/1969 | Kelley | C07C 5/08 208/142 |
| 3,492,220 A | 1/1970 | Lempert | |
| 3,494,859 A | 2/1970 | Parker | |
| 4,113,603 A | 9/1978 | Bauer | |
| 2008/0223753 A1* | 9/2008 | Picard | C10G 29/205 208/57 |

FOREIGN PATENT DOCUMENTS

| GB | 1301019 A | 12/1972 |
|---|---|---|
| GB | 1316080 A | 5/1973 |

* cited by examiner

*Primary Examiner* — Sharon Pregler
*Assistant Examiner* — Alyssa L Cepluch

(57) ABSTRACT

Methods and apparatuses are provided for producing hydrocarbons. A method for producing hydrocarbons may include two or more reactors having a distributed aromatic rich feed and hydrogen system. Using this configuration, the aromatic rich feed and hydrogen streams are split equally to all reactors wherein each reactor contains a catalyst. The outlet from the last reactor may include a recycle that may be injected into the inlet of the first reactor.

11 Claims, 1 Drawing Sheet

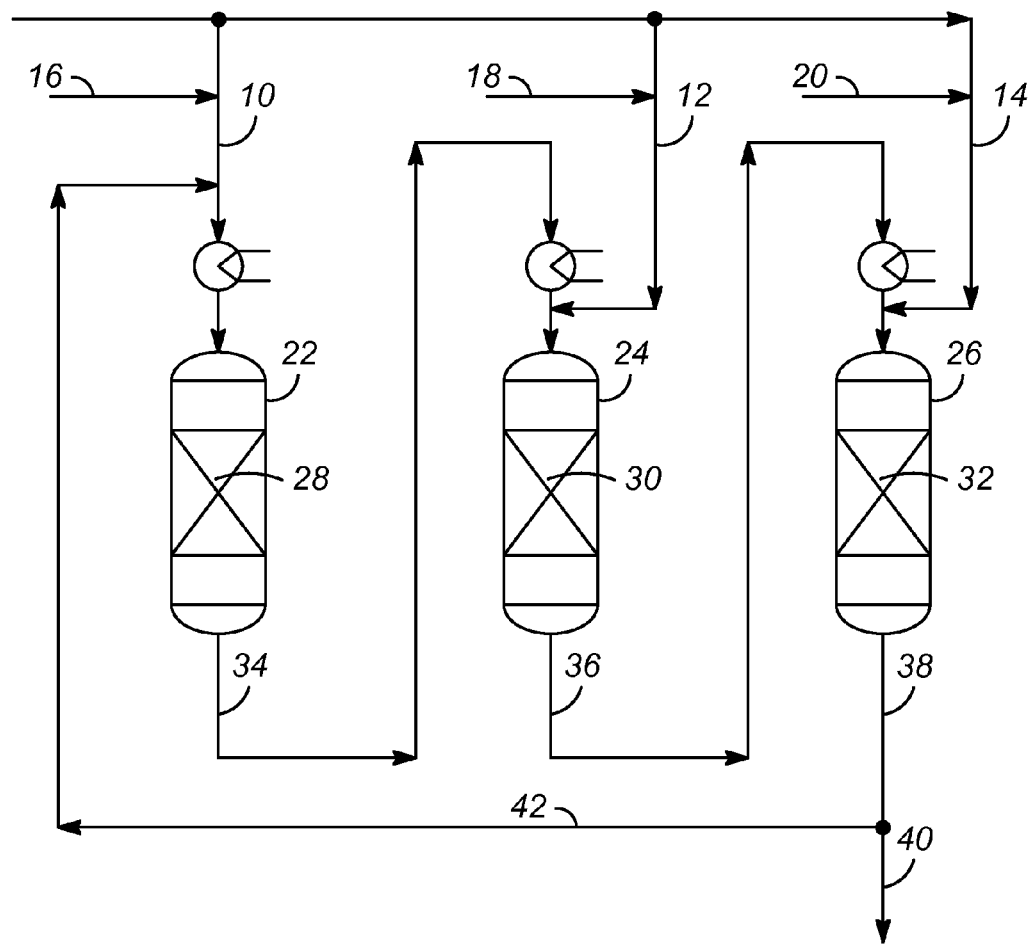

METHODS AND APPARATUSES FOR HYDROCARBON PRODUCTION

FIELD

The present subject matter relates generally to methods and apparatuses for hydrocarbon production. More specifically, the present subject matter relates to methods and apparatuses for first stage di-olefin saturation.

BACKGROUND

Streams rich in aromatics including diolefins are often formed as by-products of hydrocarbon conversion processes. For example, Pyrolysis gasoline is often obtained as a by-product from thermal cracking of various hydrocarbons. The pyrolysis gasoline often includes many aromatic compounds, as well as diolefins (hydrocarbons with two sets of double bonds), mono-olefins (hydrocarbons with one double bond), alkanes with no double bonds, and sulfur and nitrogen compounds. Depending on the feed source to the thermal cracker, pyrolysis gasoline may also contain metal contaminants. Pyrolysis gasoline can be used as a source for aromatic compounds, but the diolefins, mono-olefins, sulfur and nitrogen compounds need to be removed before the aromatic compounds can be recovered by various processes, such as solvent extraction.

The pyrolysis gasoline is often treated in a two-step process prior to separating and purifying the aromatic compounds. This application addresses improvements to only the first step of the process. In the first step, diolefins and any alkynes are selectively hydrogenated to form mono-olefins and some paraffins. The first step is operated under moderate conditions with a selective catalyst such that primarily diolefins are reacted to mono-olefins. At the same time some of the mono-olefins are saturated and very few, if any, aromatic compounds are saturated. In the second step, additional mono-olefins are saturated (hydrogenated) to form alkanes, and the nitrogen and sulfur compounds are removed. The second step is operated under more severe reaction conditions, in the presence of a selective catalyst that would cause diolefins to polymerize and undesirably result in reactor pressure drop issues, therefore the first step is used to remove the more reactive diolefins prior to the second step.

The first step is operated at moderate conditions with a selective catalyst, so diolefins are reacted to mono-olefins, but relatively few mono-olefins are saturated and essentially no aromatic compounds saturated. The diolefins are far more reactive than the mono-olefins and aromatic species. The first step is often operated at a reactor inlet temperature of about 50 to about 150° C. with a delta temperature of up to about 20-50° C. across the reaction zone and a maximum outlet temperature of about 200 degrees centigrade (° C.) or less. The second step is often operated at an inlet temperature of about 250 to about 350° C. with about a 30-60° C. delta temperature across the reaction zone and a maximum outlet temperature of about 400° C. The diolefins and mono-olefins are hydrogenated in separate reactors, i.e. the first and second steps are conducted in separate reactors, to limit and control polymerization of the diolefins. Reducing mono-olefin hydrogenation reactions in the first stage limits excessive heat from the exothermic reaction that causes polymerization of diolefins. Over time deposit of heavy polymerate gradually accumulates and deactivates the catalyst, so periodically the catalyst needs to be hot hydrogen stripped or regenerated.

The claimed subject matter focuses on the first stage reactor section of the pyrolysis gasoline treatment process. In some examples, the configuration requires a large reactor effluent recycle stream, when high feed rates are used or if the diolefin concentration is high, or both. Hydrogen is often distributed to the first and second reactor beds in the first stage reaction section. The distributed hydrogen is used to more selectively saturate the diolefins and vinyl aromatics present in the feed. This has the potential to be hydrogen lean at the first reactor outlet and potential to create a higher temperature rise than desired if the reaction proceeds faster in the first bed than anticipated. If this occurs there is a possibility that the hydrogen lean environment can lead to polymerization type reactions which could result in plugging or shorter catalyst cycle.

Accordingly, it is desirable to develop methods and apparatuses for producing hydrocarbons. In addition, it is desirable to develop methods and apparatuses for reducing the reactor recycle rate by better utilizing the reactor effluent stream as a diluent for temperature control. Furthermore, other desirable features and characteristics of the methods and apparatus described herein will become apparent from the subsequent detailed description and the appended claims, taken in conjunction with the accompanying drawings and this background.

SUMMARY

Methods and apparatuses for producing hydrocarbons are provided. By one aspect, a method for producing hydrocarbons may include two or more reaction zones having a distributed feed and hydrogen system. Using this configuration, the feed and hydrogen are split equally to all reaction zones. The distribution of feed, hydrogen, and recycle may be varied depending on the feed and process objectives. The outlet from the last reaction zone may include a recycle that may be injected into the inlet of the first reaction zone. However it is also contemplated that the final reaction zone outlet may be injected in between the reaction zones as well.

An advantage of the methods and apparatuses for hydrocarbon production is that having several reactors reduces the recycle rate by better utilizing the reactor effluent recycle stream as a diluent for temperature control.

Another advantage of the methods and apparatuses for hydrocarbon production is that having several reactors offers better control and flexibility of the system.

Another advantage of the methods and apparatuses for hydrocarbon production is that having several reactors results in a more favorable recycle to feed ratio for a typical hydrocarbon feed. The recycle reduces the reactor inlet concentration of very reactive diolefin types present in the fresh feed.

A further advantage of the methods and apparatuses for hydrocarbon production is that having several reactors results in a recycle reduction of 40% to 80% from the original design depending on the feed rate, feed composition, and number of reactors utilized.

Yet another advantage of the methods and apparatuses for hydrocarbon production is that the distributed flow scheme offers positive control of the reactor temperature rise, and the flow scheme allows for a slight excess of hydrogen in the reactor effluent.

Another advantage of the methods and apparatuses for hydrocarbon production is that the distributed flow scheme is that the reactor temperature can be adjusted as needed to maintain the diene conversion by analyzing the reactor effluent for dienes and or vinyl aromatics.

Additional objects, advantages and features will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations.

The FIGURE is a schematic diagram of an apparatus and a method for producing hydrocarbons using a liquid recycle, cooling, distributed feed, and distributed hydrogen system in accordance with various embodiments.

DETAILED DESCRIPTION

The following detailed description is merely exemplary in nature and is not intended to limit the application and uses of the embodiment described. Furthermore, there is no intention to be bound by any theory presented in the preceding background or the following detailed description.

The various embodiments described herein relate to methods and apparatuses for producing hydrocarbons having a distributed feed and hydrogen system. Diolefins in an aromatic rich feed stream are reacted with hydrogen in the presence of a catalyst to produce mostly mono-olefins in a reactor effluent stream. Some of the reactor effluent stream recycled while the rest is fractionated in a fractionation zone to produce a C-5 stream, a C6-8 stream, and a C9+ stream, where the letter "C" represents carbon, and the following number represents the number of carbon atoms present in the molecule.

With reference to the FIGURE, an aromatic rich feed stream is distributed to each of a plurality of reactors. In the example illustrated in the FIGURE there are three reactors, so there are three aromatic rich feed streams. A first aromatic rich feed stream 10 is fed into a first reactor 22. The first reactor 22 is configured to contain a first catalyst 28. The first aromatic rich feed stream 10 includes C4-10 hydrocarbons, such that about 20 percent or more by one approach, about 50 percent or more by another approach, and about 90 mass percent or more by yet another approach of the first aromatic rich feed stream 10 is hydrocarbons with 4 to 10 carbon atoms. The first aromatic rich feed stream 10 includes about 20 mass percent or more aromatic compounds, so it is rich in aromatic compounds. The first aromatic rich feed stream 10 may include a pyrolysis gasoline produced by steam cracking variety of feed types including light alkanes, naphtha, distillates, and gas oils. The first aromatic rich feed stream 10 may also include other or additional sources, such as a coke oven light oil, wash oil, etc.

As illustrated in the FIGURE there are three reactors, however, it should be understood that there may be two or more reactors. The number of reactors may vary depending, for example, on the feed flow rates and composition of the aromatic rich feed streams and the hydrogen supply streams. The number of aromatic rich feed streams and hydrogen supply streams may correspond to the number of reaction zones in the systems. For example, if there are two reactors, there will be two aromatic rich feed streams and two hydrogen supply streams. However, if there are three reactors, as illustrated in the example in the FIGURE, there will be three aromatic rich feed streams and three hydrogen supply streams. Also, it may be possible to have a large reactor having two reaction zones where feed and hydrogen may be distributed separately as well.

Also, as illustrated in the FIGURE, the reactors are proportionate to each other in size, so as to accommodate and equally split amount of aromatic rich feed streams, hydrogen supply streams, and catalysts. However, it is contemplated that according to various approaches the reactors may be different sizes, as the amount of aromatic rich feed streams, hydrogen supply streams, and the amount of catalysts needed to produce the desired hydrocarbons may vary. As illustrated in the FIGURE, the three reactors are in series.

The first aromatic rich feed stream 10 includes aromatic compounds, and often includes about 30 to about 90 mass percent aromatic compounds. The first aromatic rich feed stream 10 also includes at least one of diolefins and mono-olefins, saturates (hydrocarbons without double or triple bonds between adjacent carbon atoms) sulfur and/or nitrogen compounds, and may include some alkynes, and metal contaminants. The components of the aromatic rich feed stream may vary widely. For example, where the aromatics rich feed stream 10 include a pyrolysis gasoline stream, the feedstock and operating conditions in a steam cracker that produces pyrolysis gasoline varies widely, so the components of the pyrolysis gasoline stream vary widely. As an example, one pyrolysis gasoline first aromatic rich feed stream 10 included about 28 mass percent C5-compounds, about 59 mass percent C6-8 compounds, and about 13 mass percent C9+ compounds, where about 49 mass percent of the entire stream was aromatic compounds, 26 mass percent was diolefins, about 9 mass percent was mono-olefins, and about 16 mass percent was saturates. In this example the feed contained about 5 wppm sulfur and about 20 wppm nitrogen. As mentioned above, the concentration of the various components in the first aromatic rich feed stream 10 can vary significantly from the example described above.

Also, as mentioned above, by one aspect, at least a portion of the first aromatic rich feed stream 10, a portion of the second aromatic rich feed stream 12, and a portion of the third aromatic rich feed stream 14 are drawn from a common aromatic rich feed stream. However, it should be understood that the at least portion of the first aromatic rich feed stream 10, a portion of the second aromatic rich feed stream 12, and a portion of the third aromatic rich feed stream 14 may be drawn from different aromatic rich feed streams.

By one aspect, as illustrated in the FIGURE, a first hydrogen supply stream 16 is fed to the first reactor 22 and provides hydrogen gas. The first aromatic rich feed stream 10 contacts the first catalyst 28 in the first reactor 22 in the presence of hydrogen, where at least a portion of the diolefins are catalytically hydrogenated to form mono-olefins. At least a portion of alkynes in the feed stream 16 are also reacted to form mono-olefins, and some olefins may be reacted to form saturates. Aromatic compounds include more than 2 sets of double bonds, but aromatic compounds are more stable than diolefins so relatively few to none of the aromatic compounds in the aromatic rich feed stream 10 are hydrogenated in each reactor. Low temperatures are preferably used in the reactors, which produces mild reaction conditions, with temperatures ranging from about 40 to about 200° C. In an exemplary embodiment, the inlet temperature is about 40 to about 60° C., and the outlet temperature is about 120 to about 150° C. The reaction pressure can vary, such as from about 2,000 kilopascals (kPa) to about 7,000 kPa in one example, from about 2000 to 6000 in another example, and from about 3000 to 4000 in yet another example. The liquid hourly space velocity (LHSV) of the first aromatic rich feed stream 10 can also vary over a wide range. Typically, the LHSV will be in the range of about 0.5 to about 30 liters of the first aromatic rich feed stream 10 per liter of catalyst per hour. However, the LHSV may be in the range of about 1.0 to about 10 liters of the first aromatic rich feed stream 10 per liter of catalyst per hour. The temperature, pressure, hydrogen addition rates, and LHSV variables are controlled to avoid significant hydrogenation of mono-olefins.

By one aspect, as illustrated in the FIGURE, the hydrogen supply streams are equally split between the plurality of reactors, for example the first reactor 22, the second reactor 24, and the third reactor 26. By another aspect, the hydrogen supply streams between the first reactor and the second reactor 24 may be split into various ratios between the plurality of reactors, depending on the aromatic rich feed stream composition and flow rate. For example, instead of an equal amount of hydrogen supply streams entering between the first reactor 22, the second reactor 24, and the third reactor 26, hydrogen distribution and addition rates may be varied. There is a possibility that one would like to also saturate some or all of the olefins and so more hydrogen up front may be desired to increase the hydrogen to hydrocarbon ratio. There is a possibility that more hydrogen will be required in the later reactors. Another possibility is the need to run the last reactor as a polishing reactor where one would require additional saturation and so more hydrogen would be needed.

Also, as illustrated in the preferred embodiment in the FIGURE, the aromatic rich feed stream and the hydrogen supply stream are split proportionate to the number of rectors. However, it is contemplated that in alternative embodiments, only the hydrogen supply stream may be split to control the reaction rate. For example, the aromatic rich feed stream and the hydrogen supply stream may be admixed with the recycle stream from the previous reactor before entering the next reactor, or the aromatic rich feed stream and the hydrogen supply stream may enter the reactor at distinct inlets. This process flow configuration also allows independent temperature and hydrogen addition control to each reactor section. This will allow for adjustments to be made to the process if the processing objectives change. As a example, if the di-olefin content of the feed increases, the hydrogen rate can be adjusted to account for this. Also if required, the hydrogen addition rate to the last reactor can be increased to ensure the di-olefins are saturated as the catalyst ages, with only a slight loss of selectivity in the first stage.

There is the possibility that the fresh feed to each RX systems will not be split evenly. For example there is the possibility that one would process more fresh feed up front and less fresh feed in the subsequent reactors. This may be done to assure that most of the conversion is done up front and the more difficult reaction types are done in the bottom reactor. There is also the possibility that the catalyst amounts will not be split evenly. For example there is the possibility that one load the reactor such that the catalyst volume increases with each subsequent reactor. This may be done to assure that the most difficult type of reactions have the necessarily residence time to meet target product quality. In the example illustrated in the FIGURE there is a first catalyst 28, a second catalyst 30, and a third catalyst 32, in the three separate reactors, however they catalysts may be the same. Here, the catalysts selectively catalyze hydrogenation of diolefins and alkynes to produce mono-olefins and some olefins to saturates, but have little catalytic activity for hydrogenation of aromatic compounds at the reaction conditions in the reactors. In an exemplary embodiment, the catalysts include a metal from group 10 of the periodic table of elements (nickel, palladium, and platinum), and a support. The group 10 metal can be in one of several forms, such as in the metal form, oxide form, or sulfide form. In some embodiments, the catalysts also include one or more other metals or metal compounds, such as a metal or metal compound from groups 8 and/or 9 and/or 11 of the periodic table of elements (iron, ruthenium, osmium, cobalt, rhodium, iridium, copper, silver, and gold), and/or one or more alkali metals which may include an acidity modifier. Any of the metals may be sulfided, where the metal is reacted with sulfur to form a metal sulfide.

The support can be any of a wide variety of materials, such as aluminum oxide, silicon oxide, titanium oxide, zirconium oxide, aluminum phosphate, scandium oxide, yttrium oxide, magnesium oxide, silica, aluminosilicates (clays, zeolites), activated carbon, and combinations thereof. In some embodiments, the support includes one or more aluminum oxide (alumina), such as alpha-alumina, theta-alumina, gamma-alumina, boehmite, diaspore, bayerite and/or pseudoboehmite. The support is alkali treated in some embodiments to remove acidity. Particles of the catalysts can have many shapes, including but not limited to spherical, cylindrical, granular, and trilobal, and the catalyst particle size can vary widely as well, such as from an average size of about 0.1 to about 100 millimeters (mm), as a length or diameter.

In the embodiment illustrated in the FIGURE, the catalysts are the same in the first reactor 22, the second reactor 24, and the third reactor 26. However, it is contemplated that in alternative embodiments, there may be different catalysts in each of the first reactor 22, the second reactor 24, and the third reactor 26, or two or the reactors may contain the same catalyst, and only one reactor may contain a different catalyst. For example, the catalysts may vary in that they may include a variety of different metals and supports that are previously mentioned.

In the embodiment illustrated in the FIGURE, a first reactor effluent stream 34 exits the first reactor 22, where the first reactor effluent stream 34 primarily includes mono-olefins, alkanes, and aromatic compounds. There are very few if any diolefins and alkynes in the first reactor effluent stream 34, such as less than about 1 mass percent but may be adjusted to desired conversion level. As shown in the FIGURE, a portion of the first reactor effluent stream 34 may enter the second reactor 24, along with the second aromatic rich feed stream 12 and the second hydrogen supply stream 18.

As discussed previously, a portion of the first reactor effluent stream 34 may enter the second reactor 24, along with the second aromatic rich feed stream 12 and the second hydrogen supply stream 18. The second reactor 24 contains a second catalyst 30. The second aromatic rich feed stream 12 contacts the second catalyst 30 in the second reactor 24 in the presence of hydrogen, where at least a portion of the diolefins are catalytically hydrogenated to form mono-olefins. At least a portion of alkynes in the feed stream 12 are also reacted to form mono-olefins, and some olefins may be reacted to form saturates. In the embodiment illustrated in the FIGURE, a second reactor effluent stream 36 exits the second reactor 24, where the second reactor effluent stream 36 primarily includes mono-olefins, alkanes, and aromatic compounds. There are very few if any diolefins and alkynes in the second reactor effluent stream 36, such as less than about 1 mass percent but may be adjusted to desired conversion level. As shown in the FIGURE, a portion of the second reactor effluent stream 36 may enter the third reactor 26, along with the third aromatic rich feed stream 14 and the third hydrogen supply stream 20.

In the embodiment illustrated in the FIGURE, a third reactor effluent stream 38 then exits the third reactor 26, where the third reactor effluent stream 38 primarily includes mono-olefins, alkanes, and aromatic compounds. There are very few if any diolefins and alkynes in the third reactor effluent stream 38, such as less than about 1 mass percent but may be adjusted to desired conversion level. As shown in the FIGURE, a portion of the third reactor effluent stream 38 exits as the product stream 40, and the other portion of the third reactor effluent stream 38 may be the recycle stream 42. The recycle stream 42 may enter the first reactor 22, along with the first aromatic rich feed stream 10 and the first hydrogen supply stream 16. However, it is also contemplated that in alternative embodiments, the recycle stream 42 may also be injected into any other reactors as well. For example, the recycle stream 42 may enter the inlet of the second reactor 24, or the third reactor 26, or the recycle stream 42 may enter all of the reactors.

The product stream 40 may be fractionated in a fractionation zone to produce various fractions for further processing or use, so the reactors may be coupled to a fractionation zone.

The product stream 40 may be cooled at any point after exiting the third reactor 26. Normally there is considerable temperature rise from the inlet to the outlet of the reactor catalyst bed when saturating diolefins. A specific temperature rise and or limit are desired from inlet to outlet to maintain target conversion, selectivity, and stability. The temperature rise for each reactor is controlled by the recycle and cooling. Cooling is needed on the reactor effluent product so to obtain a desired inlet temperature to the subsequent reactor. Cooling can be installed on the recycle stream or the combined recycle plus effluent stream. Cooling of the recycle only stream is done to cool the upstream reactor effluent so that the combined stream going to the subsequent reaction is at the desired inlet temperature. Cooling on the combined recycle and reactor effluent stream can also be done for the desired inlet temperature to the subsequent reaction.

As discussed above, it is important to control the temperature rise across the process. This ensures the maximum selectivity and minimizes fouling of the catalyst. The typical way to control the reaction zone temperature rise is to recycle some of the reactor effluent which dilutes the reactive di-olefins to a lower concentration so that the required temperature control is achieved. As discussed previously, when a large amount of feed is used, a large recycle is produced. By using the claimed process, the recycle stream may be reduced by 40-80%. For the feed used in the current example, the feed contains 26 wt % di-olefins. In one example, in order to effectively control the reaction zone change in temperature, the recycle to feed ratio would be in the range of 9:1. Using the split feed design, this recycle rate would be reduced to 3.1:1.

The catalytic reaction of diolefins with hydrogen produces deposits that adhere to the catalysts, and the deposits may adhere to the walls of the reactors as well. Without being bound to any particular theory, it is believed that the catalytic reaction of diolefins with other diolefins produces a heavy polymerate, which includes a polymer formed from the diolefins or other compounds in the aromatic rich feed streams. The deposits form gradually, and deactivate the catalysts as the deposits accumulate on the catalysts. The deposits may not be soluble in the aromatic rich feed streams at the temperature in the reactors during the diolefin hydrogenation reaction, so the deposits accumulate. At some point, the activity of the catalysts is reduced to the point where the catalysts need to be regenerated. For example, the catalysts may be regenerated when the catalysts activity degrades to the point where a temperature of the reactor effluent streams exiting the reactors reaches set point limit. The set point limit is usually determined by the type of dienes present in the feed. Alternatively, the catalysts may be regenerated when the pressure drop across the reactors increases beyond a set limit. Other criteria can also be used to determine when to regenerate the catalysts.

A further advantage to having more than one reactor is that individual reactors may be designed to be shut down to perform processes to remove the deposits on the catalyst. When there is only a single reactor operating, that reactor must be shut down so that the process stops running while the catalyst in that reactor is stripped. Therefore the entire process shuts down while this process is performed. However when there are multiple reactors being used to perform the process, as there are in the claimed invention, the process does not have to be shut down. The remaining system can run at a reduced throughput or the severity can be increased on the remaining reactors to maintain certain product quality.

For example, in the preferred embodiment illustrated in the FIGURE, only the first reactor 24 may be shut down to strip deposits from the first catalyst 30. In this example if only the first reactor 24 may be shut down to strip deposits from the first catalyst 30, the second reactor 22 and the third reactor 26 may continue to run without the first reactor 24, so the process may continue while the catalyst in each reactor can be stripped at different times. An example of processes used to remove deposits from a catalyst would be hot hydrogen stripping, which removes the soft coke from a catalyst. Another advantage of having more than one reactor is that the catalyst is divided up amongst the reactors. For example, in the preferred embodiment illustrated in the FIGURE, since the reactors contain only one third of the total catalyst, the equipment used to remove the deposits from the catalyst, such as hot hydrogen stripping equipment, will be three times smaller than if the entire inventory of catalyst had to be stripped at the same time.

It should be noted that various changes and modifications to the presently preferred embodiments described herein will be apparent to those skilled in the art. Such changes and modifications may be made without departing from the spirit and scope of the present invention and without diminishing its attendant advantages.

The invention claimed is:

1. A method of producing hydrocarbon compounds comprising:
    splitting an aromatic rich feed into a first aromatic rich feed stream comprising diolefins and a second aromatic rich feed stream comprising diolefins;
    feeding the first aromatic rich feed stream comprising diolefins, a first hydrogen rich stream, and a recycle stream to a first reaction zone comprising a first catalyst to form a first effluent stream comprising mono-olefins, wherein the recycle stream is cooled; and
    feeding the second aromatic rich feed stream comprising diolefins, a second hydrogen rich stream, and first effluent stream, wherein the first effluent stream is cooled and sent to a second reaction zone comprising a second catalyst to form a second effluent comprising mono-olefins wherein a portion of the second effluent stream may be recycled to the first reaction zone, the second reaction zone, or both the first reaction zone and the second reaction zone, the first and second reaction zones having an inlet temperature of about 40° C. to about 60° C. and an outlet temperature is about 120° C. to about 150° C., wherein the first reaction zone and the second reaction zone comprise independent temperature control.

2. The method of claim 1 wherein the first reaction zone and the second reaction zone are connected in series.

3. The method of claim 1 wherein the first reaction zone and the second reaction zone may include multiple reactors.

4. The method of claim 1 wherein the first aromatic rich feed stream, the first hydrogen stream, and the recycle stream are admixed before being fed to the first reaction zone and the second aromatic rich feed stream, the second hydrogen stream, and the first effluent stream are admixed before being fed to the second reaction zone.

5. The method of claim 1 wherein the flow rate of the first hydrogen stream and the second hydrogen stream may be controlled independently.

6. The method of claim 1, wherein at least a portion of the first aromatic rich feed stream and at least a portion of the second aromatic rich feed stream are drawn from a common aromatic rich feed stream.

7. The method of claim 1, further comprising feeding a third aromatic rich feed stream comprising diolefins, a third hydrogen rich stream, and a second effluent stream to a third reaction zone comprising a third catalyst to form a third reaction zone effluent stream comprising mono-olefins.

8. The method of claim 1 wherein the first catalyst comprises a metal from group 10 of the periodic table, and wherein the first catalyst further comprises a support selected from one or more of aluminum oxide, silicon oxide, titanium oxide, and zirconium oxide.

9. The method of claim 1 wherein the first catalyst and the second catalyst comprise palladium on an aluminum oxide support.

10. The method of claim 1 wherein the first catalyst and the second catalyst comprise nickel on an aluminum oxide support.

11. The method of claim 1 wherein the second catalyst comprises a metal from group 10 of the periodic table, and wherein the second catalyst further comprises a support selected from one or more of aluminum oxide, silicon oxide, titanium oxide, and zirconium oxide.

* * * * *